(12) United States Patent
Faherty

(10) Patent No.: US 6,517,507 B1
(45) Date of Patent: Feb. 11, 2003

(54) WRIST GUARD FOR ALLEVIATING REPETITIVE STRAIN DISORDER BY COMPUTER OPERATORS

(76) Inventor: Caron Faherty, 2104 NW. 22 Ave., Stuart, FL (US) 34994-8801

( * ) Notice: Subject to any disclaimer, the term of this patent is extended or adjusted under 35 U.S.C. 154(b) by 10 days.

(21) Appl. No.: 09/710,384

(22) Filed: Nov. 13, 2000

Related U.S. Application Data

(63) Continuation-in-part of application No. 09/246,155, filed on Feb. 8, 1999.

(51) Int. Cl.[7] .............................. A61F 5/00; A61F 13/00
(52) U.S. Cl. ........................................... 602/64; 602/21
(58) Field of Search ....................... 602/20–21, 60–64, 602/5; 128/878–879; D24/190

(56) References Cited

U.S. PATENT DOCUMENTS 3,322,118 A  *  5/1967  Sotherlin .................... 602/60
5,329,638 A  *  7/1994  Hansen ........................ 2/16
5,769,808 A  *  6/1998  Matthijs ..................... 602/64
5,887,277 A  *  3/1999  Lohman ........................ 2/16

* cited by examiner

Primary Examiner—Denise M. Pothier
(74) Attorney, Agent, or Firm—Ronald E. Greigg

(57) ABSTRACT

A support device which is worn on one's wrist to protect the median nerve when the wrist is resting on a surface such as a keyboard of a computer. The device is tubular in structure and fabricated of a knit material including a mixture of SPANDEX® and cotton. The knit material permits the tubular device to expand for placing the device over the hand and onto the wrist. The tubular knot material includes a pocket or space in which a foam material is placed. The foam ends are folded back toward each other and spaced from each other to form a canal. The canal is placed toward the wrist when worn and aligned with the median nerve. Therefore, a space is provided over the median nerve to protect the median nerve from excess pressure from the wrist.

5 Claims, 2 Drawing Sheets

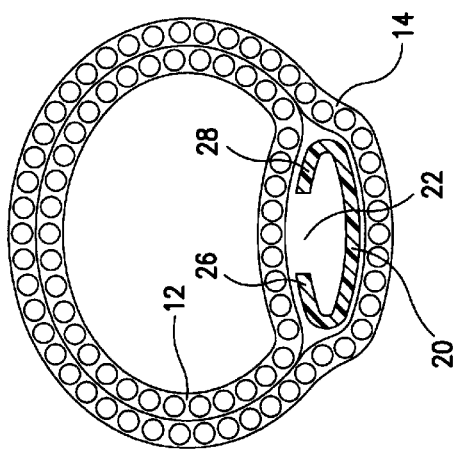
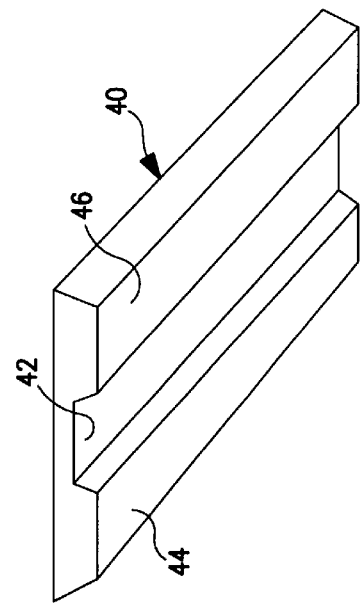
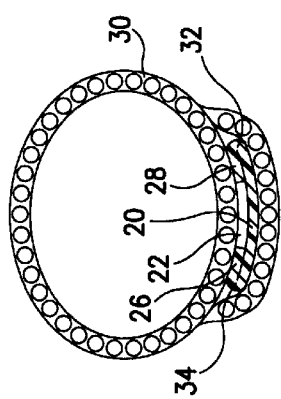
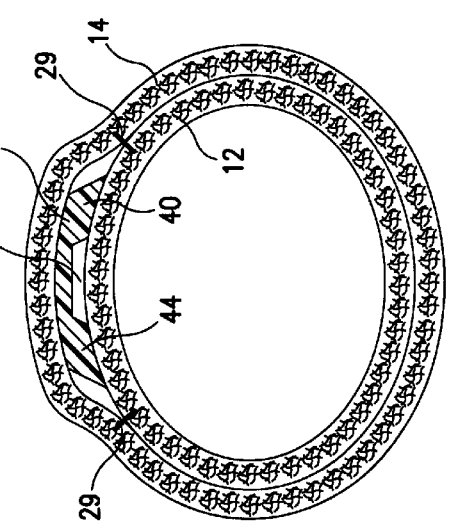

WRIST GUARD FOR ALLEVIATING REPETITIVE STRAIN DISORDER BY COMPUTER OPERATORS

CROSS REFERENCE TO RELATED APPLICATIONS

This is a continuation-in-part of corresponding application Ser. No. 09/246,155 filed on Feb. 8, 1999.

FIELD OF THE INVENTION

This invention is directed to a device for protecting one's wrist to alleviate the potential for injury to the median nerve caused by constant pressure on the intracarpal canal.

BACKGROUND OF THE INVENTION

It has been determined that many computer keyboard operators are not trained typists who were trained so their hands would float over the keys. The typist's hands were to be held in a natural position and their hand had to do small amounts of exercise with loading/rolling the paper, returning the carriage, etc. Computer operators must rest their wrists on a keyboard or a pad while holding their hands in extension. A wrist, without a supportive device, can exert up to 90 mm pressure while in full extension. Sunderland suggest the impairment of the median nerve goes from venous congestion to anoxic endothelial damage to impaired blood supply and hypoxia (Sunderland, S. The Nerve Lesion in the Canal Tunnel Syndrome, J. Neural Neurosurg Psychiatry 1976, 39:61526).

Edema of the nerve further accelerates the rise in pressure and vascular compromise worsens. Over time, nerve injury results in irreversible axonal degeneration, fibrosis and demyelination. The poor outcomes of surgical correction at this stage are a disappointment to all (Ref Gelberman, R.H. et al, "Carpal Tunnel Syndrome". A Scientific Basis for Clinical Care. Ortho Clin Namer Jan. 19, 1988 (1):115–24).

Fransson-Hull & Kilbom conducted a systematic study of the pain threshold patterns for the hand. They showed that the pain increased with greater duration and intensity of the pressure and that some of the parts of the hand were more sensitive to pressure than others, e.g., the median nerve being one. Applied Ergonomics 24 (3):181–189,1993.

SUMMARY AND OBJECTS OF THE INVENTION

This invention is directed to a wrist support that protects the intracarpal canal from exertional pressure without decreasing functional mobility. This device does not encroach on the mobility of the forearm, thumb or wrist in any plane of motion, yet provides neutral warmth as well as providing the protective tunnel for the median nerve.

Cosmetically, the device appears similar to an athletic type wrist band or sweat band. It is comfortable to wear, non-restrictive, but with support when needed to keep pressure off the median nerve. As it appears more athletic in nature, the psychological component may increase wearing compliance. It is not intended to take the place of medical treatment; however, it does not require a prescription and can be utilized by wise consumers to prevent repetitive stress disorders. It is easy to slip over the hand and to line up the tunnel with the center of the hand, palm up, and retains its position during use without restricting hand or wrist movement.

The device is lightweight, one size fits all (though not recommended for wrist greater than about 10"). It is not cumbersome, it can be worn while preforming tasks other than keyboarding, including recommended hand exercises. There is no left or right discrimination, speeding up set up time. There are no straps or closures, as in common in the prior art devices, and the device does not restrict functional mobility in any plane of motion.

It is therefore an object of the invention to provide a wrist support which will keep pressure off the median nerve while resting the wrist on a surface.

Another object is to provide a wrist device which is comfortable to wear, which is lightweight and easy to position on the wrist.

Still another object is to provide a device in which one size fits all up to a certain size wrist.

Other objects and advantages of the invention will become obvious to those skilled in the art upon an understanding of the invention as shown by the drawings and described in the disclosure.

BRIEF DESCRIPTION OF THE DRAWINGS

FIG. 5, is a cross sectional view of an alternative embodiment of the device;

FIG. 6, is a cross sectional view of a further alternative embodiment;

FIG. 7, is a cross sectional view of a further alternative embodiment; and

FIG. 8, is an enlarged perspective view of the foam insert employed in FIG. 7.

DETAILED DESCRIPTION

Figure 2:
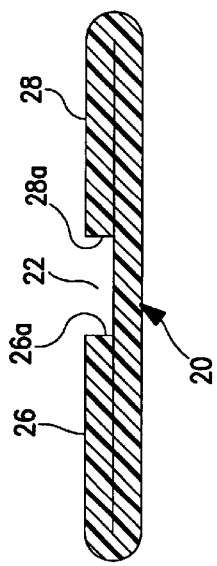
FIG. 2, is a cross sectional view of the foam material insert employed in FIG. 1 to form a tunnel for protecting the median nerve.
Figure 4:
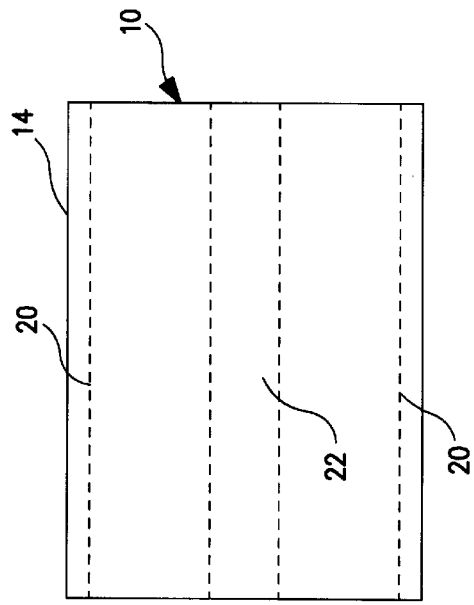
FIG. 4, is a side view of the device.
Figure 1:
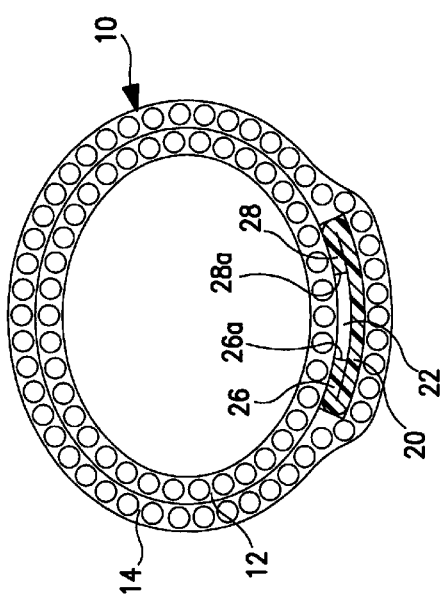
FIG. 1, is a cross sectional view of one embodiment of the device illustrating the relative parts.
Figure 3:
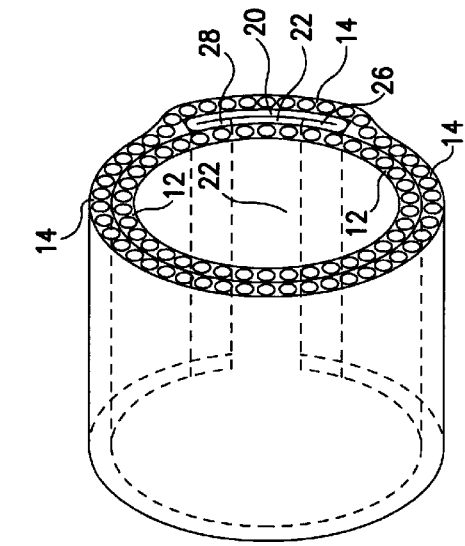
FIG. 3, is a perspective view illustration the device with the foam material insert.

Now referring to the drawings wherein the reference characters refer to the same parts throughout the drawings, there is shown in FIG. 1 a median nerve protecting device 10 in accordance with one embodiment of the invention. The device is fabricated form a tubular type of material or fabric comprising from 2 to 3 percent SPANDEX® mixed with a 97 to 98 percent cotton knitted into the tubular configuration. The tubular material in a normal or relaxed state has about a 5 inch inside circumference measurement which can be stretched to comfortably fit up to about a 10 inch circumference wrist without exerting an excess pressure on the intracarpal canal, that is, a pressure no more than 15 mm pressure. The device can be made by using a continuous tubular knit material cut into a length of about 5 inches and folded back into itself to form a space between the inner and outer layers 12 and 14, respectively. A generally rectangular piece of foam sheet 20 having portions 26, 28 along opposed parallel sides folded back onto one surface with the edges 26a and 28a spaced from one another to define a canal 22 having a width of from about ½ to about ¾ inches and a depth equal to the thickness of the foam sheet. The folded edge portion can be held in place by sewing, gluing or other suitable means. The piece of foam with the folded edge portions is positioned between the two layers 12, 14 of material with the folded portion contacting the inner surface of layer 12 with the canal extending along the width of the knit material as shown in FIGS. 3 and 4. The knit material extends over the open channel 22 to form a tunnel, with the porous absorbent material permitting air flow through the material allowing the skin to breathe when the device is in use.

The foam is secured in place between the fabric layers 12, 14 with channel 22 parallel to the longitudinal axis of the tubular material by any suitable means. For example, the tubular material can be sewn along opposite sides of the foam as shown at 29 in FIG. 7 in order to form a pocket, or the outwardly directed surface of the foam may be bonded to the inner surface of layer 14 to assure that the tunnel is properly aligned along the length of the tubular member tunnel.

In an alternative embodiment illustrated in FIG. 5, a length of an absorbent tubular knit fabric 30, preferably fabricated of SPANDEX® and cotton material as described above, has a second partial layer 32 attached to its outer surface, as by sewing, to form a pocket 34 in which the foam 20 is positioned.

It is believed apparent that pocket 34 could also be attached on the interior as shown in FIG. 6.

In a further embodiment, illustrated in FIGS. 7 and 8, the soft foam element 40 may be formed from a generally rectangular section of a foam sheet or strip initially having a uniform thickness, and subsequently having an elongated groove or channel 42 formed in one face surface thereof as by cutting or skiving, leaving thickened edge portions 44, 46. Alternatively, the element 40 may be molded, extruded or otherwise formed with the channel 42 initially formed therein. For example, a continuous strip having a cental channel formed therein and extending along its length can be cut into length as required to form the individual foam elements 40. The foam elements are secured in the fabric sleeve or pocket in the same manner as the folded foam element described above.

In each of the modifications, once the foam has been set in place the open end through which the foam is inserted can be sewn to close the opening. For the modifications in which the tubular form is folded back onto itself, FIG. 1, the entire circumference where the ends of the fold meet can be sewn together after the foam is in place. It would be obvious that the end circumference could be sewn except for an opening through which the foam is placed and subsequent to positioning the foam in place, the remainder of the end circumference could be sewn together. In any event, the pocket or confined space within which the foam element is secured is of a size such that the fabric extends over the open tunnel to close the channel 22, forming a closed tunnel. The size of the pocket and of the soft foam insert are such that the inwardly directed surface of the inner layer 12 of fabric contacts the skin of the wearer in the area extending over the tunnel. As pressure is applied to the device by the wearer resting the wrist on a surface, the thicker edge portions of the foam will be compressed without applying pressure to the median nerve until the edges have collapsed a distance equal to the depth of the tunnel. Thereafter, the portion of the foam at the tunnel bottom will be compressed, but less pressure will be applied to the median nerve until the foam is completely collapsed.

A support device as set forth above can be inexpensively fabricated and can be made in any desirable colors or of different colors. The band could be made with one's initials and/or with a company's logo or any other feature desired.

In use of the support device, it is placed over the hand with the palm up. The foam formed canal 22 or 44 will be facing the palm of the hand and is to fit along the median nerve to prevent excess pressure on this area. The support devices are made of a tubular material and the channel extends the full length of the foam so there is no right or left; the device can be worn on either wrist. The device preferably has the tubular covering material formed of an absorbent cotton/spandex blend; therefore, the material will provide a neutral warmth to the wrist and has open cells which minimizes perspiration. Further, the wrist is not inhibited from moving in any particular motion and will permit the wearer to perform other tasks and can perform hand exercises to assist in prevention of repetitive trauma disorders.

In order to assure that the tunnel is lined-up properly on the wrist, some type of mark can be made on the outer surface of the support which would relate to the tunnel. The support could then be lined-up with the mark over the median nerve.

The foregoing relates to preferred exemplary embodiments of the invention, it being understood that other variants and embodiments thereof are possible within the spirit and scope of the invention, the latter being defined by the appended claims.

I claim:

1. A wrist support for encompassing and supporting the wrist of a wearer to alleviate pain resulting from conditions such as carpal tunnel syndrome, the support comprising, an elongated, tubular covering formed from an absorbent, stretchable fabric and having an inner and an outer layer and a longitudinal axis, a pad of soft foam material disposed between said inner and outer layers, said pad being generally rectangular and having opposed generally parallel side edges oriented parallel to the longitudinal axis of said elongated tubular covering, and generally flat inner and outer surfaces respectively, disposed in contact with said inner and outer layers, respectively, an elongated channel formed in said inner surface and extending the full length of said pad at a location substantially equally spaced from said side edges, said channel having a depth at least about half the distance between said inner and outer surfaces, said inner layer extending over said elongated channel and cooperating therewith to form an elongated tunnel adapted to face the wrist of a person wearing the support with the tunnel aligned with the carpal tunnel of a person wearing the wrist support and with the inner layer adapted to contact the wrist along the carpal tunnel, and means securing said pad between said inner and outer layers to retain the relative orientation of said pad and said tubular covering.

2. The wrist support defined in claim 1, wherein said inner and outer layers of fabric are joined together to define a pocket therebetween, said pad being positioned within said pocket to retain said side edges oriented generally parallel to said longitudinal axis.

3. The wrist support defined in claim 2, wherein said pad is formed from a generally rectangular sheet of soft foam material, said sheet having opposed parallel side edge portions with each of said edge portions being folded over to form two pairs of surfaces which face each other, and said pairs of facing surfaces being secured to each other, said folded side edge portions being spaced from one another to define said channel.

4. The wrist support defined in claim 2, wherein one of said layers is in the form of an elongated knitted tubular fabric, and the other layer is a separate piece of knitted fabric secured to said one layer and extending over and covering said pad and defining said pocket.

5. The wrist support defined in claim 2, wherein said channel is in the form of an elongated groove formed in one surface of a single layer of a sheet of foam having a substantially uniform thickness on opposed sides of said channel.

* * * * *